(12) United States Patent
Fjield et al.

(10) Patent No.: US 6,763,722 B2
(45) Date of Patent: Jul. 20, 2004

(54) ULTRASONIC TRANSDUCERS

(75) Inventors: Todd Fjield, Shoreham, NY (US); Patrick David Lopath, Setauket, NY (US); Edward Paul Harhen, Duxbury, MA (US)

(73) Assignee: Transurgical, Inc., Setauket, NY (US)

(*) Notice: Subject to any disclaimer, the term of this patent is extended or adjusted under 35 U.S.C. 154(b) by 111 days.

(21) Appl. No.: 09/904,620

(22) Filed: Jul. 13, 2001

(65) Prior Publication Data

US 2003/0013968 A1 Jan. 16, 2003

(51) Int. Cl.$^7$ .............................................. G01N 29/00
(52) U.S. Cl. ......................................... 73/644; 73/579
(58) Field of Search .......................... 73/644, 589, 590, 73/579, 1.48, 64.53, 591, 1.68; 310/327, 334

(56) References Cited

U.S. PATENT DOCUMENTS

| | | | |
|---|---|---|---|
| 4,084,582 A | | 4/1978 | Nigam |
| 4,194,510 A | | 3/1980 | Proudian |
| 4,387,720 A | | 6/1983 | Miller |
| 4,680,499 A | * | 7/1987 | Umemura et al. .......... 310/334 |
| 4,685,334 A | * | 8/1987 | Latimer ....................... 73/599 |
| 4,691,714 A | * | 9/1987 | Wong et al. ................ 600/551 |
| 4,800,316 A | * | 1/1989 | Ju-Zhen ...................... 310/327 |
| 4,841,977 A | | 6/1989 | Griffith et al. |
| 5,105,116 A | * | 4/1992 | Okamoto et al. ........... 310/311 |
| 5,240,005 A | | 8/1993 | Viebach |
| 5,246,438 A | | 9/1993 | Langberg |
| 5,305,755 A | | 4/1994 | Nakao |
| 5,421,338 A | | 6/1995 | Crowley et al. |
| 5,423,319 A | | 6/1995 | Seyed-Bolorforosh |
| 5,454,782 A | | 10/1995 | Perkins |
| 5,477,736 A | | 12/1995 | Lorraine |
| 5,488,955 A | | 2/1996 | Dias |

(List continued on next page.)

FOREIGN PATENT DOCUMENTS

| | | |
|---|---|---|
| WO | WO98/52465 | 11/1998 |
| WO | WO99/02096 | 1/1999 |
| WO | WO 99/44519 | 10/1999 |
| WO | WO 00/51511 | 9/2000 |
| WO | WO 00/51683 | 9/2000 |
| WO | WO 00/67648 | 11/2000 |
| WO | WO 00/67656 | 11/2000 |

OTHER PUBLICATIONS

U.S. patent application Ser. No. 09/435,281.

U.S. patent application Ser. No. 09/281,727.

U.S. patent application Ser. No. 09/233,337.

U.S. Provisional patent application Ser. No. 60/133,677.

U.S. Provisional patent application Ser. No. 60/073,477.

U.S. Provisional patent application Ser. No. 60/218,641.

Zipes, Douglas P., M.D., Catheter Ablation of Arrhythmias, 1994.

(List continued on next page.)

Primary Examiner—Hezron Williams
Assistant Examiner—Jacques M. Saint-Surin
(74) Attorney, Agent, or Firm—Lerner, David, Littenberg, Krumholz & Mentlik, LLP

(57) ABSTRACT

A compact, high-power ultrasonic emitting transducer has an active element such as a piezoelectric element and structure defining a reflective backing interface such as an air interface behind the rear surface of the active element. A liquid is provided in the resonant unit between the backing interface and the active element.

24 Claims, 2 Drawing Sheets

U.S. PATENT DOCUMENTS

| | | | |
|---|---|---|---|
| 5,513,639 A | | 5/1996 | Satomi et al. |
| 5,575,766 A | | 11/1996 | Swartz et al. |
| 5,582,609 A | | 12/1996 | Swanson et al. |
| 5,596,989 A | | 1/1997 | Morita |
| 5,606,974 A | | 3/1997 | Castellano |
| 5,620,479 A | | 4/1997 | Diedrich |
| 5,630,837 A | | 5/1997 | Crowley |
| 5,637,683 A | | 6/1997 | Sanghui |
| 5,655,539 A | | 8/1997 | Wang et al. |
| 5,704,361 A | | 1/1998 | Seward et al. |
| 5,720,287 A | | 2/1998 | Chapelon et al. |
| 5,762,066 A | | 6/1998 | Law et al. |
| 5,840,031 A | | 11/1998 | Crowley |
| 5,848,969 A | | 12/1998 | Panescu et al. |
| 5,916,170 A | | 6/1999 | Kolz et al. |
| 5,971,983 A | | 10/1999 | Lesh |
| 6,012,457 A | | 1/2000 | Lesh |
| 6,055,859 A | * | 5/2000 | Kozuka et al. ............... 73/570 |
| 6,094,988 A | * | 8/2000 | Aindow ...................... 73/649 |
| 6,106,474 A | | 8/2000 | Koger et al. |
| 6,117,101 A | | 9/2000 | Diederich et al. |
| 6,164,283 A | | 12/2000 | Lesh |
| 6,193,713 B1 | | 2/2001 | Geistert et al. |
| 6,196,059 B1 | * | 3/2001 | Kosslinger et al. ........ 73/61.49 |
| 6,197,023 B1 | | 3/2001 | Muntermann |
| 6,282,949 B1 | * | 9/2001 | Axelsson ................... 73/64.53 |
| 6,513,385 B1 | * | 2/2003 | Han et al. ...................... 73/629 |
| 6,543,274 B1 | * | 4/2003 | Herrmann et al. .......... 73/32 A |

OTHER PUBLICATIONS

Volkmer, Marius, M.D., "Focal Atrial Tachycardia from Deep Inside the Pulmonary Veins", 1997.

Swartz, John F., "A Catheter–based Curative Approach to Atrial Fibrillation in Humans", 1994.

Hatala, Robert, "Radiofrequency Catheter Ablation of Left Atrial Tachycardia Originating Within the Pulmonary Vein in a Patient with Dextrocardia", 1996.

Reuter, David, M.D., "Future Directions of Electrotherapy for Atrial Fibrillation,"1997.

Mallavarapu, Christopher, "Radiofrequency Catheter Ablation of Atrial Tachycardia with Unusual Left Atrial Sites of Origin," 1996.

Haissaguerre, Michel, M.D., "Right and Left Atrial Radiofrequency Catheter Therapy of Paroxysmal Atrial Fibrillation," 1996.

Jais, Pierre, M.D., "A Focal Source of Atrial Fibrillation Treated by Discrete Radiofrequency Ablation," 1996.

Robbins, Ivan, M.D., "Pulmonary Vein Stenosis After Catheter Ablation of Atrial Fibrillation," 1998.

Haissaguerre, Michel, M.D., "Predominant Origin of Atrial Panarrhythmic Triggers in the Pulmonary Veins: A Distinct Electrophysiologic Entity," 1997.

Haissaguerre, Michel, M.D., "Spontaneous Initiation of Atrial Fibrillation by Ectopic Beats Originating in th Pulmonary Veins," 1998.

Prager, Nelson, A., "Long Term Effectiveness of Surgical Treatment of Ectopic Atrial Tachycardia," 1993.

Haissaguerre, Michel, M.D., "radiofrequency Catheter Ablation in Unusual Mechanisms of Atrial Fibrillation," 1994.

Kay, G. Neal, "Radiofrequency Ablation for Treatment of Primary Atrial Tachycardia," 1993.

Tracy, Cynthia M., "Radiofrequency Catheter Ablation of Ectopic Atrial Tachycardia Using Paced Activation Sequence Mapping," 1993.

Scheinman, Melvin, M., NASPE Survey on Catheter Ablation, 1995.

Walsh, Edward P., M.D., "Transcatheter Ablation of Ectopic Atrial Tachycardia in Young Patients Using Radiofrequency Current," 1992.

Feld, Gregory K., "Radiofrequency Catheter Ablation for the Treatment of Human Type I Atrial Flutter," 1992.

Swartz, John, F., M.D., "Radiofrequency Endocardial Catheter Ablation of Accessory Atrioventricular Pathway Atrial Insertion Sites," 1993.

Lesh, Michael, D., M.D., "Radiofrequency Catheter Ablation of Atrial Arrhythmias," 1994.

Van Hare, George, F., "Radiofrequency Catheter Ablation of Supraventricular Arrhythmias in Patients With Congenital Heart Disease: Results and Technical Considerations," 1993.

Chintz, Larry, A., "Mapping Reentry Around Atriotomy Scars Using Double Potentials," 1996.

Liem, L. Bing, "In Vitro and In Vivo Results of Transcatheter Microwave Ablation Using Forward–Firing Tip Antenna Design," 1996.

Montenero, Sandro, Annibale, "Electrograms for Identification of the Atrial Ablation Site During Catheter Ablation of Accessory Pathways," 1996.

Cosio, Francisco, G., "Atrial Flutter Mapping and Ablation II." 1996.

O'Connor, Brian, K., "Radiofrequency Ablation of a Posteroseptal Accessory Pathway Via the Middle Cardia Vein in a Six–Year Old Child," 1997.

Gallagher, John, J., "Wolff–Parkinson–White Syndrome: Surgery to Radiofrequency Catheter Ablation," 1997.

Hsieh, Ming–Hsiung, M.D., "Double Multielectrode Mapping Catheters Facilitate Radiofrequency Catheter Ablation of Focal Atrial Fibrillation Originating from Pulmonary Veins," 1998.

Hocini, Meleze, "Multiple Sources Initiating Atrial Fibrillation from a Single Pulmonary Vein Identified by a Circumferential Catheter," 2000.

Kumagai, Koichiro, "Treatment of Mixed Atrial Fibrillation and Typical Atrial Flutter by Hybrid Catheter Ablation," 2000.

Lesh, M.D., An Anatomic–Approach to Prevention of Atrial Fibrillation: Pulmonary Vein Isolation with Through–the-–Balloon Ultrasound Ablation (TTB–US), 1999.

Haissaguerre, Michel, "Electrophysiological End Point for Catheter Ablation of Atrial Fibrillation Initiated From Multiple Venous Foci," 1999.

Hocini, Meleze, "Concealed Left Pulmonary Vein Potentials Unmasked by Left Atrial Stimulation," 2000.

Chen, Shih–Ann, M.D., "Intiation of Atrial Fibrillation by Ectopic Beats Originating From the Pulmonary Veins," 1999.

Moubarak, Jean, B., "Pulmonary Veins–Left Atrial Junction: Anatomic and Histological Study," 2000.

Lin, Wei–Shiang, M.D., "Pulmonary Vein Morphology in Patients with Paroxysmal Atrial Fibrillation Initiated by Ectopic Beats Originating From the Pulmonary Veins," 2000.

Igawa, Osamu, "The Anatomical Features of the Junction between the Left Atrium and the Pulmonary Veins: The Relevance with Atrial Arrhythmia,".

* cited by examiner

ULTRASONIC TRANSDUCERS

FIELD OF THE INVENTION

The present application relates to ultrasonic transducers.

BACKGROUND OF THE INVENTION

Ultrasonic transducers are used for a wide variety of applications including imaging, nondestructive testing and heating. For example, in certain medical procedures ultrasonic energy is applied to heat tissue within the body of a living subject. In an ablation procedure, the tissue is heated sufficiently to kill undesired tissue as, for example, to about 60–80 degrees C. In ablation and similar procedures, it is highly desirable to heat the undesired tissue rapidly, so as to minimize collateral damage to neighboring tissue. Certain ablation techniques use ultrasonic transducers which are inserted into the body as, for example, on a catheter. Such transducers must be compact, but should be capable of emitting substantial ultrasonic power.

A typical ultrasonic transducer includes an active element such as a piezoelectric or magnetostrictive element. The active element physically deforms in response to an applied drive signal, most commonly an electrical signal. In operation, the active element is driven by a signal at an ultrasonic driving frequency and produces ultrasonic vibrations. The transducer may consist only of the active element, but typically includes additional structural elements. The active element and these additional structural elements are arranged to form a composite structure which resonates at the driving frequency. The vibrations from this structure are emitted into the surrounding medium. For example, in a typical medical application, the ultrasonic vibrations are emitted from the transducer into a liquid or gel medium and are transmitted through this medium into the tissue.

Typically, the transducer is arranged to emit acoustic vibrations from a front surface into the surrounding medium. The transducer typically has one or more acoustically reflective interfaces remote from the front surface, and typically to the rear of the active element. The interface or interfaces help to direct the ultrasonic energy out of the transducer through the front surface. As further discussed below, the term "backing interface" is used to refer to an interface which plays a significant part in the operation of the transducer. The resonant unit includes the structure between the backing interface furthest from the front or emitting surface and the emitting surface.

Some transducers employ a solid backing element having acoustic impedance different from the acoustic impedance of the active element. For example, a transducer incorporating a polymeric piezoelectric active element may include a solid backing element formed from a metal or ceramic. The interface between the backing element and the polymeric active element serves as a backing interface.

Other transducers, referred to as "air-backed" transducers, have a structure which provides an air layer at the rear surface of the active element. For example, as shown in U.S. Pat. No. 5,620,479, the interior bore of a tubular ceramic element is filled with air. The interface between the air and the element is highly reflective, because air has an acoustic impedance far lower than that of the ceramic. This interface serves as a backing interface, and helps to direct acoustic vibrations through the outer surface of the tubular element, which serves as the front or emitting surface of the transducer.

Air-backed transducers can provide good efficiency and can be compact. However, the emitting power of such a transducer is limited by thermal considerations. Air and other gasses provide only a limited cooling effect at the rear surface of the active element. The power of the applied drive signal must be limited to avoid overheating the transducer. This problem is particularly severe in the case of small transducers for applications such as ablation.

Thus, despite the considerable effort applied heretofore in development of ultrasonic transducers, further improvement is needed.

SUMMARY OF THE INVENTION

The present invention addresses these needs.

One aspect of the present invention provides an ultrasonic transducer. The transducer in accordance with this aspect of the invention includes a resonant unit which in turn includes an active element having a front surface facing in a forward direction and having a rear surface facing in a rearward direction. The active element may be a piezoelectric element or other element operative to generate ultrasonic vibrations in response to an applied signal. The resonant unit includes a liquid disposed to the rear of said active element. For example, the liquid may be in contact with the rear surface of the active element. The resonant unit is resonant at an ultrasonic frequency and adapted to emit ultrasonic vibrations principally in said forward direction.

A further aspect of the invention provides an ultrasonic transducer including an active element having front and rear surfaces. Here again, the active element is operative to generate ultrasonic vibrations in response to an applied signal. The transducer further includes a rear structure defining a space disposed to the rear of said active element. A liquid is disposed in this space. The element, rear structure and liquid cooperatively form a resonant unit having a backing interface. The liquid is disposed between the backing interface and the rear surface of the active element. In a particularly preferred arrangement, the rear structure may include a wall having a front surface facing toward the space and a rear surface facing away from the space. A medium such as a gas having acoustic impedance lower than the acoustic impedance of the liquid abuts the rear surface of the wall to form a backing interface.

A transducer according to a further aspect of the invention includes an active element, rear structure and liquid as discussed above. In this aspect of the invention, the liquid partially defines a backing interface of the transducer. For example, the rear structure may include a solid wall to the rear of the space, the wall having acoustic impedance differing from the acoustic impedance of the liquid, so that the interface between the liquid and the wall serves as a backing interface.

Preferred transducers in accordance with these aspects of the present invention are compact and efficient. However, because the liquid ss disposed within the resonant unit it can provide efficient cooling for the active element. The transducer desirably includes or is connected to a source of liquid arranged to move the liquid through the space. The most preferred transducers according to these aspects of the invention can provide output power higher than the power provided by an air-backed transducer of comparable size. Merely by way of example, a cylindrical, tubular transducer in accordance with one preferred embodiment is less than 3 mm in diameter but can provide over 50 Watts of continuous acoustic output power at about 9 MHz when operated in water. The preferred transducer according to the foregoing aspects of the invention can be use in various applications. For example, such transducers are especially valuable in ultrasonic ablation devices for insertion into the body of a subject.

Other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 4:
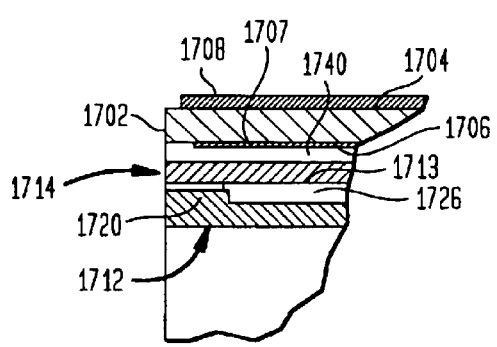
FIG. 4 is a fragmentary view on an enlarged scale of the area indicated in FIG. 2.

An ultrasonic transducer or emitter in accordance with a preferred embodiment of the invention is depicted in FIGS. 1–4. The emitter includes an active piezoelectric element 1702 in the form of a thin cylindrical tube having an exterior or front surface 1704 and an interior or rear surface 1706. An electrode 1708 forms the front surface 1704 of the piezoelectric element, and a similar electrode 1707 forms the rear surface. The thickness of the electrode is greatly exaggerated in FIGS. 2 and 4 for clarity of illustration. In practice, the electrode preferably is formed by a thin metallic coating, such as a plated or sputtered coating of metal on the order of a few thousand Angstroms thick overlying the actual piezoelectric material. An internal structure 1710 includes an inner support tube 1712 and an outer support tube 1714. Support tubes 1712 and 1714 desirably are formed from a metallic, electrically conductive material. As best seen in FIG. 4, inner support tube 1712 has an outwardly projecting shoulder 1720 at one end. A similar shoulder 1722 is provided at the opposite end. Outer support tube 1714 has a cylindrical internal bore. Shoulders or rings 1720 and 1722 fit closely within the cylindrical bore of the outer support tube. Thus, over the major portion of the length of the support structure, between shoulders 1720 and 1722, there is a gap 1726 between the inner surface of outer support tube 1714 and the outer surface of inner support tube 1712. The tubes are sealed to one another at shoulders 1720 and 1722. Gap 1726 is filled with a gas, such as normal room air, at the time the tubes are sealed to one another. This gas remains permanently within gap 1726.

Figure 1:
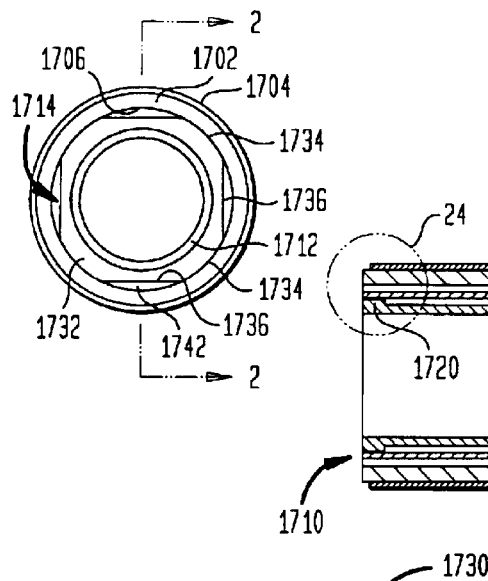
FIG. 1 is an end view of a transducer according to one embodiment of the invention.
Figure 2:
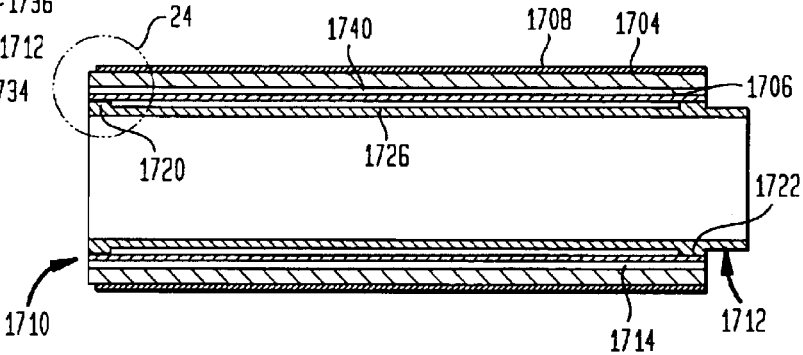
FIG. 2 is a sectional view of the transducer of FIG. 1.
Figure 3:
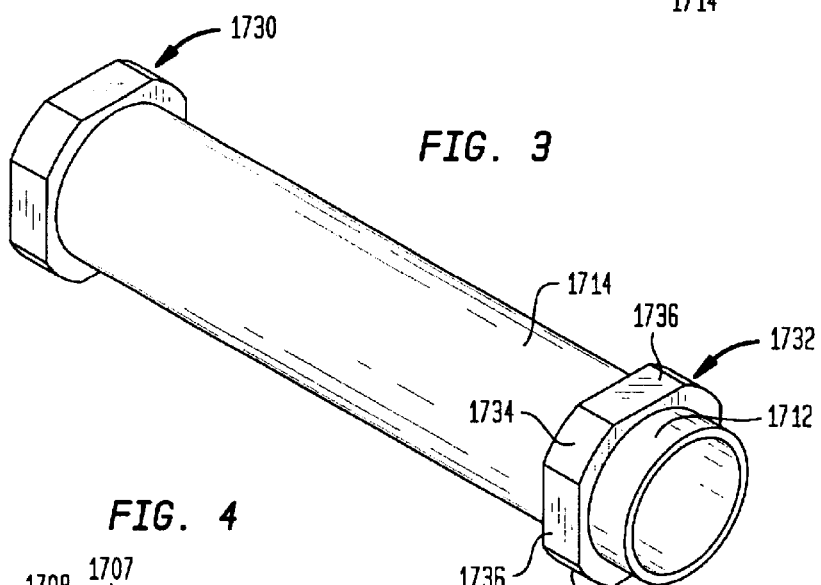
FIG. 3 is a perspective view of a part of the transducer of FIGS. 1 and 2.

Outer support tube 1714 has a pair of outwardly projecting shoulders 1730 and 1732 at the ends of the outer support tube. Each shoulder has arcuate surfaces 1734 connected by flats 1736, so that each shoulder is generally in the form of a square with rounded corners. The arcuate surfaces 1734 are concentric with the main portion of the support tube 1714. Seen in end view, the flats 1736 are tangent to the cylindrical surface of the main portion of the support tube. As best seen in FIG. 1, the tubular piezoelectric electric element 1702 is supported on the arcuate surfaces 1734 of shoulders 1732 and 1730, so that the inner surface 1706 of the piezoelectric element is concentric with the outer surface of support tube 1714, but is spaced apart from the support tube so as to define a space in the form of a tubular passageway 1740 between the outer support tube and the inner or rear surface 1706 of the piezoelectric element. Passageway 1740 is open to the exterior of the transducer through small gaps 1742 defined between the inner surface 1706 of the piezoelectric element and the flats 1736 of the shoulders on the outer support tube.

In operation, the space or passageway 1740 is filled with a liquid. The front surface of the emitter (the front surface 1704 of the active piezoelectric element) is acoustically coupled to the medium which is to receive ultrasonic energy from the emitter.

For example the emitter of FIGS. 1–4 may be used as the ultrasonic emitte in the apparatus described in copending, commonly assigned Unted States Patent Application of Todd Fjield et al. entitled Thermal Treatment Methods And Apparatus With Focused Energy Application filed of even date herewith, now U.S. Pat. No. 6,635,054, the disclosure of which is hereby incorporated by reference herein. Also, the emitter of FIGS. 1–4 may be used in the copending, commonly assigned United States Patent Application of Paul Harhen et al. entitled Energy Application With Inflatable Annular Lens, also filed of even date herewith, the disclosure of which is hereby incorporated by reference herein.

Figure 5:
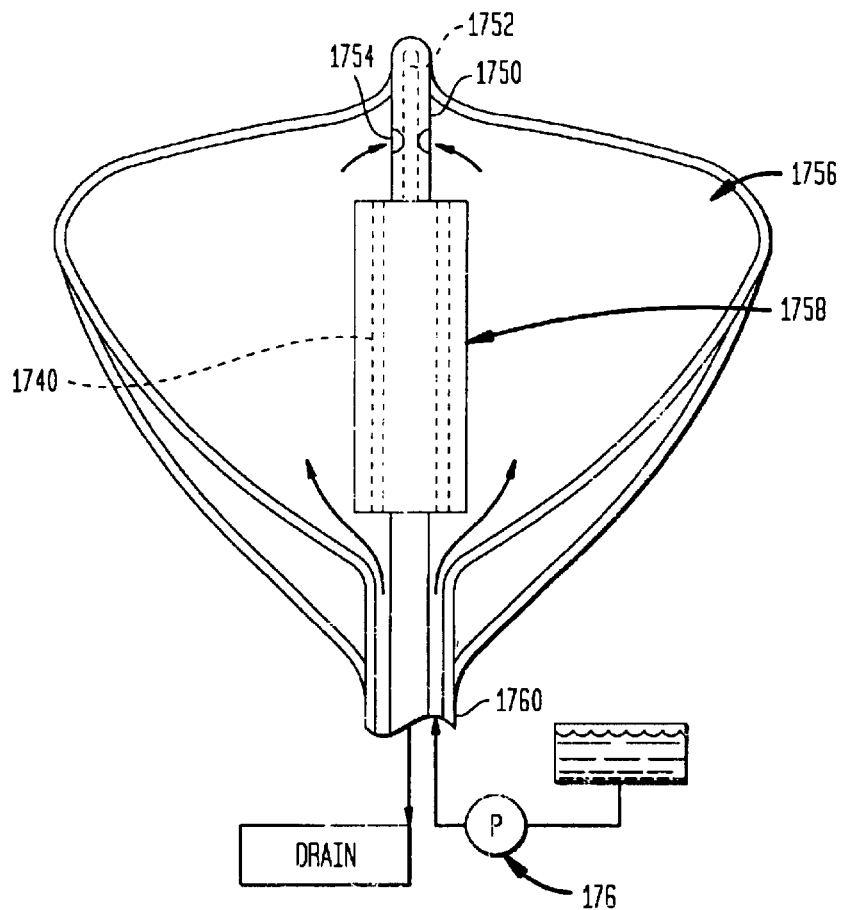
FIG. 5 is a fragmentary sectional view of apparatus incorporating the transducer of FIGS. 1–4.

One apparatus incorporating the emitter of FIGS. 1–4 is shown in FIG. 5. This apparatus includes a probe structure incorporating a carrier catheter 1760, a structural balloon 1756 having a proximal end connected to the carrier catheter, and a guide catheter 1750 extending through the lumen of the carrier catheter into or through structural balloon 1756. Guide catheter 1750 has an internal lumen 1752 and one or more ports 1754 communicating with the interior space of the structural balloon 1756 adjacent the distal end of this balloon and distal to the transducer or emitter 1758. The lumen of the carrier catheter is connected to a source 1761 of a liquid such as an aqueous liquid as, for example, water or saline solution, whereas the lumen of guide catheter 1750 is connected to a drain. The liquid source may include conventional fluid-handling elements as, for example, a reservoir containing a liquid and a pump or gravitational feed arrangement to convey the liquid through the system. The liquid is admitted from carrier catheter 1760 adjacent the proximal end of the balloon through an annular opening close to the proximal end of the transducer, so that the liquid flows generally in the distal direction. A significant portion of the flowing liquid will pass through the passageway or space 1740 within the transducer. The source and drain connections may be reversed to provide the opposite flow, with liquid admitted through ports 1754 and passing out through the proximal end of the balloon into carrier catheter 1760. Also, the drain may be connected to feed the source, so that the liquid continually recirculates. Additionally, a baffle structure may be provided to direct more of the flowing liquid through passageway 1740. At one extreme, the emitter may be sealingly connected to the carrier catheter 1760 or to the guide catheter 1752, so that liquid can only enter the structural balloon through the passageway 1740 of the emitter, or so that liquid can only leave the structural balloon through passageway 1740. In this manner, all of the fluid passing through the structural balloon is directed through the passageway 1740. In the arrangement of FIG. 29, the front surface of the emitter is in contact with the liquid in the balloon 1756 so that the emitter can radiate ultrasonic energy into the liquid into the balloon; the liquid in the balloon serves as the medium coupled to the front surface of the emitter.

The air or other gas in gap 1726 (FIGS. 2 and 4) forms a highly-reflective interface 1713 with the metallic material of the outer support tube 1714.

The reflectivity of an interface between two materials is determined mainly by the acoustic impedances of the materials on opposite sides of the interface. The reflectivity of the interface is given by the formula:

$$R=(Z_1-Z_2)/(Z_1+Z_2)$$

where:
R is the reflectivity of the interface;
$Z_1$ is the acoustic impedance of the material on one side of the interface; and
$Z_2$ is the acoustic impedance of the material on the other side of the interface.

Acoustic impedance is sometimes described as the acoustic velocity or speed of sound in a medium multiplied by the density of the medium. More accurately, acoustic impedance is defined as the acoustic pressure divided by the volume velocity. Volume velocity is the velocity that the particles in the medium are moving. Because wall 1714 is quite thin, the reflectivity of interface 1713 is determined in part by the acoustic impedance of the liquid in space 1740, and, to some degree, by the acoustic impedance of the material in wall 1714. Typical aqueous fluids have acoustic impedance of about 1.5 MRayls, whereas typical gases have acoustic impedance of less than about $10^{-4}$ Mrayls. The acoustic impedance of solids such as the metal in wall 1714 is far higher than that of typical gases. The reflectivity at the interface 1713 typically is at least about 0.9 and more typically nearly 1.0.

In operation, the emitter is excited by an electrical potential applied between electrodes 1707 and 1708. This potential is applied at a predetermined ultrasonic drive frequency as, for example, about 1–15 MHz. The potential may be applied through electrical conductors (not shown) extending between the proximal end of the probe structure and the emitter, using a conventional ultrasonic-frequency driver (not shown). The reflective interface at surface 1713 (FIGS. 2 and 4) and the outer surface 1704 of the emitter, and the stack of materials between these surfaces, constitute a resonant unit. As the piezoelectric material is excited, it repeatedly grows and shrinks in the forward-to-rearward direction of the stack, i.e., in the direction between surfaces 1704 and 1706. The ultrasonic vibrations propagate through the stack, and are reflected forwardly at the interfaces within the stack and by the interface at surface 1713, at the inner or rear surface of the stack. The dimensions of the various layers in the interior of the stack, between surfaces 1713 and 1704 (including the liquid layer within space 1740) are selected so that the unit is resonant at the drive frequency, and so that the acoustic vibrations are emitted from the resonant unit principally through the front surface 1704 into the medium coupled to the front surface. That is, more energy passes through the interface 1704 at the outer or front surface of the stack than through interface 1713. Although there is some reflectivity at interfaces within the stack, as at the interfaces bounding the liquid passageway 1740, the reflective interface 1713 is effectively exposed to the ultrasonic vibrations in the stack and, thus, plays a substantial role in directing emissions to the front of the stack. The liquid within passageway 1740 effectively cools the piezoelectric element and other elements of the stack. Thus, the transducer element 1702 is cooled at both its front surface and its rear surface. This is in marked contrast to a conventional air-backed transducer. Such a transducer typically has a layer of air directly behind the rear surface of the piezoelectric element and, accordingly, has little or no heat transfer from the rear surface of the piezoelectric element. Surprisingly, an emitter in accordance with this embodiment of the invention can convert electrical power to acoustic power radiated into the surrounding medium through the front surface with an efficiency equal to the efficiency of an air-backed emitter. The emitter according to this embodiment of the invention, however, provides this efficiency in conjunction with better heat transfer and, hence, can operate at substantially higher power levels than the equivalent air-backed transducer of the same size.

The materials and dimensions of the various layers in the resonant unit desirably are optimized to assure maximum efficiency at the desired operating frequency. Conventional modeling techniques may be employed for such optimization. One such technique is the well-known KLM Model described in Krimholtz et al., "New Equivalent Circuits for Elementary Piezoelectric Transducers," Electronics Letters, Vol. 6, No. 13, pp. 398–399, Jun. 25, 1970, the disclosure of which is hereby incorporated by reference herein. The various layers can be modeled as one-dimensional elements, with the only dimension corresponding to the dimension in the forward-to-rearward direction of the stack, i.e., the radial dimension in the embodiment of FIGS. 1–4. More accurate modeling can be provided by finite element analysis, or by physical testing. In the emitter of FIGS. 1–4, the liquid in space or passageway 1740 forms an integral part of the resonant unit.

As discussed above, a resonant unit includes a front or principal emitting surface and includes one or more reflective interfaces disposed to the rear of the emitting surface. A reflective interface which plays a substantial role in directing the acoustic energy out of the emitting surface is referred to in this disclosure as a reflective interface which provides a backing for the resonant unit. Thus, if the reflectivity of a particular interface disposed rearwardly of the emitting surface substantially affects the efficiency of the emitter, as where an arbitrary increase or decrease in the reflectivity of 50% or more could increase or decrease the efficiency of the emitter at its resonant frequency by 15% or more, that interface should be taken as a backing interface. A resonant unit can include one or more backing interfaces. The resonant unit also includes the materials disposed between the backing interface furthest to the rear and the front or emitting surface. Materials disposed to the rear of the most rearward backing interface do not form part of the resonant unit as considered herein. For example, the inner support tube 1712 and materials disposed inside the inner support tube are not considered part of the resonant unit. The inner support tube is effectively isolated from the ultrasonic vibrations in the resonant unit by reflective interface 1713, which constitutes the most rearward backing interface. The wall thickness of the inner support tube can be varied at will (as by reducing the inside diameter of the inner support tube) without substantially affecting the efficiency of the resonant unit.

In the special case of a resonant unit which has two oppositely-directed principal emitting surfaces, the unit can be analyzed by considering one of these emitting surfaces as the front surface.

The optimum dimensions will vary with the desired operating frequency and with the materials employed. However, one exemplary embodiment uses a tubular piezoelectric element made from a ceramic lead zirconate-titanate composition, known in the art by the designation "PZT-8." The tubular transducer has an internal diameter of 83 mils (0.083 inches; 2.1 mm) and a wall thickness of 10.5 mils (0.27 mm), so that the outer diameter of the piezoelectric element is 103 mils (2.6 mm). The outer diameter of outer support tube 1714 is 72 mils (1.8 mm); and the annular passageway 1740 has a radial thickness of 5.5 mils (0.14 mm). The outer support tube is formed from half-hard brass and has a wall thickness of 5 mils (0.13 mm). The dimension between shoulders 1720 and 1722 is 325 mils (8.25 mm), and the effective length of the transducer is 8 mm. This transducer provides peak efficiency at a driving frequency of 9 MHz. When operated at 9 MHz, the transducer provides over fifty percent (50%) efficiency at electrical power levels between 20 and 100 watts. When cooled by water flowing at a rate of a few ml per minute, the transducer has been operated for periods of several minutes or more at input power levels up to 100 watts to provide approximately 51 watts of radiated acoustic power. It is believed that the transducer can be operated at even higher power.

Figure 6:
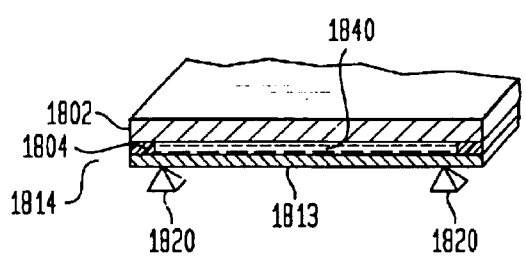
FIG. 6 is a fragmentary, diagrammatic perspective view of a transducer according to a further embodiment of the invention.

Similar stacks can be made in planar form or in any other arbitrary form. A planar emitter schematically depicted in FIG. 6 has a slab-like piezoelectric element 1802 spaced by stand-offs 1804 from a slab-like plate 1814. The plate is supported at spaced-apart locations by supports 1820. The rear surface of the plate 1813 is exposed to the atmosphere or other gas, or to another material having acoustic impedance different from that of plate 1814. A layer of liquid 1840 is provided in the space or passageway between plate 1814 and piezoelectric element 1802.

Figure 7:
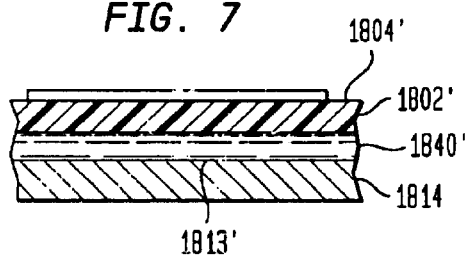
FIG. 7 is a fragmentary sectional view of a transducer according to a further embodiment of the invention.

The reflective interface at the rear or inner surface of the stack need not be an air interface. For example, as shown in FIG. 7, the emitter or transducer may include a polymeric piezoelectric material such as a PVDF material 1802', a liquid filled passageway 1840' and a steel or other thick metallic element serving as the backing. In this instance, the interface 1813' between the liquid and the metallic backing is substantially reflective. Interface 1813' serves as a backing interface of the stack. Depending upon the reflectivity at this interface, it may be desirable to provide an additional backing interface to the rear of interface 1813'. Here again, the liquid filled passageway is disposed between the piezoelectric element itself and a backing interface. In a further variant, an interface 1817' at the front surface of the liquid layer may be highly reflective. For example liquid layer 1840' may be formed from a liquid such as a liquid metal having acoustic impedance far higher than that of polymeric layer 1802', or from a liquid having low acoustic impedance.

The transducers disclosed herein can be used as emitters in essentially any application where ultrasonic power is used. Also, active elements other than piezoelectric elements can be used. The active element can vibrate in any mode; it need not vibrate in the direction between the electrodes. Where a gas is used to form an interface, it is not essential to seal the gas within an enclosed space. However, where the gas is sealed in the transducer, as in the transducer of FIGS. 1–4, the entire transducer can be exposed to liquids, as in the device of FIG. 5. There is no need to make a fluid-tight seal to the piezoelectric element. The liquid used in the space of the transducer may be the same as the medium present at the emitting surface, or may be different.

As these and other variations and combinations of the features discussed above can be employed, the foregoing description of the preferred embodiments should be taken by way of illustration rather than by way of limitation of the features discussed above.

What is claimed is:

1. A ultrasonic emitter comprising a resonant unit including an actve element having a front surface facing in a forward direction and having a rear surface facing in a rearward direction, said active element being operative to generate ultrasonic vibrations in response to an applied signal, said resonant unit including a liquid disposed to the rear of said active element, said resonant unit being resonant at an ultrasonic frequency and adapted to emit ultrasonic vibrations at said ultrasonic frequency principally in said forward direction.

2. An ultrasonic emitter comprising:

(a) an active element having a front surface facing in a forward direction and a rear surface facing in a rearward direction, said active element being operative to generate ultrasonic vibrations in response to an applied signal;

(b) a rear structure defining a space disposed to the rear of said active element,; and c) a liquid in said space, said element, said rear structure and said liquid cooperatively forming a resonant unit adapted to emit ultrasonic vibrations in said forward direction, said resonant unit including a backing interface, said liquid being disposed between said backing interface and said rear surface of said active element.

3. An ultrasonic emitter comprising:

(a) an active element having a front surface facing in a forward direction and a rear surface facing in a rearward direction, said active element being operative to generate ultrasonic vibrations in response to an applied signal;

(b) a rear structure defining a space disposed to the rear of said active element,; and (c) a liquid in said space, said active element, said rear structure and said liquid cooperatively forming a resonant unit adapted to emit ultrasonic vibrations in said forward direction, said resonant unit including a backing interface, said liquid at least partially defining said backing interface.

4. An emitter as claimed in claim 2 or claim 3, further comprising a source of liquid communicating with said space and an outlet communicating with said space, said source being operative to move said liquid through said space.

5. An emitter as claimed in claim 2 or claim 3, wherein said active element bounds said space whereby said liquid in said space is in contact with said active element.

6. An emitter as claimed in claim 3, wherein said rear structure includes a solid wall disposed to the rear of said space, said wall having acoustic impedance differing from the acoustic impedance of said liquid, said wall and said liquid cooperatively defining said backing interface.

7. An emitter as claimed in claim 2 or claim 3, wherein said rear structure includes a wall having a front surface facing toward said space and a rear surface facing away from said space, and a medium having acoustic impedance lower than the acoustic impedance of said liquid, said medium abutting said rear surface of said wall.

8. An emitter as claimed in claim 7, wherein said medium is a gas.

9. An emitter as claimed in claim 2 or claim 3, wherein said active element is a piezoelectric element.

10. An emitter as claimed in claim 9, wherein said piezoelectric element includes electrodes at said front and rear surfaces.

11. An emitter as claimed in claim 2 or claim 3, wherein said active element is generally tubular, said front surface of said active element facing to the outside of the tubular element, said space and said reflective interface being disposed within the tubular element.

12. An ultrasonic emitter comprising:
   (a) a tubular piezoelectric element having an interior bore, an inner surface bounding said bore and an outer surface;
   (b) an interior structure extending within said bore, said interior structure including a first tube substantially coaxial with said tubular piezoelectric element so that said first tube and said piezoelectric element cooperatively define an annular passageway therebetween;
   (c) a gas disposed within said first tube; and
   (d) means for connecting the annular passageway to a source of a liquid.

13. An emitter as claimed in claim 12 further comprising a sealing structure at least partially sealing said first tube and confining said gas within said first tube.

14. An emitter as claimed in claim 12 further comprising a second tube substantially concentric with said first tube, said first and second tubes cooperatively defining an annular gap therebetween, said gas being disposed in said annular gap.

15. An emitter as claimed in claim 12, wherein said first tube is formed from a metal.

16. An emitter as claimed in claim 12, wherein said tubular piezoelectric element includes a ceramic piezoelectric material.

17. An emitter as claimed in claim 12, wherein said tubular piezoelectric element has cross-sectional dimensions of 4 mm or less.

18. A method of emitting ultrasound comprising the steps of:
   (a) providing a resonant unit including an active element having a front surface facing in a forward direction, said resonant unit including a liquid disposed to the rear of said active element, said resonant unit being resonant at an ultrasonic frequency; and
   (b) driving said active element at said frequency so as to cause said active element to generate ultrasonic vibrations at said frequency, said resonant unit emitting ultrasonic vibrations principally in said forward direction.

19. A method as claimed in claim 18 further comprising the step of replacing said liquid during said driving step so that said liquid flows through said resonant unit and said liquid removes heat from said active element.

20. A method as claimed in claim 19, wherein said liquid is in contact with said active element.

21. A method as claimed in claim 18, wherein said resonant unit includes a reflective backing interface, said liquid being disposed between said reflective backing interface and said rear surface of said active element.

22. A method as claimed in claim 21, wherein said reflective backing interface includes a gas, said liquid being disposed between said gas and said rear surface of said active element.

23. A method as claimed in claim 18, wherein said resonant unit includes a reflective backing interface, and said liquid forms part of said reflective backing interface.

24. A method of emitting ultrasound comprising the steps of:
   (a) driving an active element having front and rear surfaces at an ultrasonic frequency so that said active element generates ultrasonic vibrations at said frequency;
   (b) passing a liquid through a space between the rear surface of the active element and an acoustically reflective interface so that said liquid removes heat from the active element and so that ultrasonic vibrations propagated from the rear surface of the active element pass through the liquid to the reflective interface, are reflected at the interface and pass back through the liquid to the active element, said reflective interface backing said element and directing the ultrasonic vibrations out of the element substantially through said front surface.

* * * * *

UNITED STATES PATENT AND TRADEMARK OFFICE
CERTIFICATE OF CORRECTION

PATENT NO. : 6,763,722 B2
DATED : July 20, 2004
INVENTOR(S) : Todd Fjield, Patrick David Lopath and Edward Paul Harhen It is certified that error appears in the above-identified patent and that said Letters Patent is hereby corrected as shown below:

Column 2,
Line 52, "liquid ss disposed" should read -- liquid is disposed --.
Line 63, "preferred transducer" should read -- preferred transducers --.
Line 64, "can be use" should read -- can be used --.

Column 4,
Line 13, "For example the" should read -- For example, the --.
Line 14, "ultrasonic emitte" should read -- ultrasonic emitter --.

Signed and Sealed this

Thirtieth Day of November, 2004

JON W. DUDAS
*Director of the United States Patent and Trademark Office*